United States Patent [19]

Izumi

[11] 4,295,343
[45] Oct. 20, 1981

[54] MICROBE-REMOVING AND AIR-CONDITIONING APPARATUS

[76] Inventor: Masahiko Izumi, 8,26-ban, 5-chome, Hiikawa, Nishi-ku, Fukuoka-shi, Fukuoka-ken, Japan

[21] Appl. No.: 59,184

[22] Filed: Jul. 20, 1979

[51] Int. Cl.³ ............................................. F25D 17/04
[52] U.S. Cl. ........................................ 62/309; 62/304; 55/279; 55/261; 55/263; 55/315; 261/83
[58] Field of Search .................. 62/304, 309; 55/279, 55/261, 263, 315, 282, 342, 345, 482, 267, 238, 315; 261/83; 98/30

[56] References Cited

U.S. PATENT DOCUMENTS

| | | | |
|---|---|---|---|
| 1,863,578 | 6/1932 | Morse et al. | 55/267 X |
| 2,409,088 | 10/1946 | Weits | 55/345 |
| 2,607,438 | 8/1952 | Bailey | 55/263 |
| 3,299,620 | 1/1967 | Hollingworth | 55/279 |
| 4,089,915 | 5/1978 | Jackson | 55/279 X |

Primary Examiner—Albert J. Makay
Assistant Examiner—Henry Bennett
Attorney, Agent, or Firm—Browdy and Neimark

[57] ABSTRACT

An apparatus in which air in a room such as sickroom, aseptic working room etc. is fed to an water-spraying cyclone to remove dusts and microbes and make air humid, and fed the resulting air to a temperature-regulating cyclone to remove water droplets and regulate a temperature as required, and then fed thus obtained temperature-regulated air to said room for circulation of the air through this system.

Using this microbe-removing and air-conditioning apparatus, it is possible to obtain an air of desired temperature and humidity, and at the same time supply an air from which microbes have been completely removed and which is most appropriate for sickroom, operating room etc.

2 Claims, 4 Drawing Figures

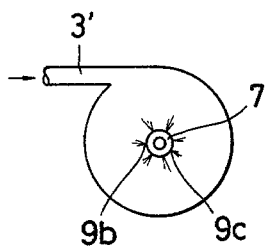
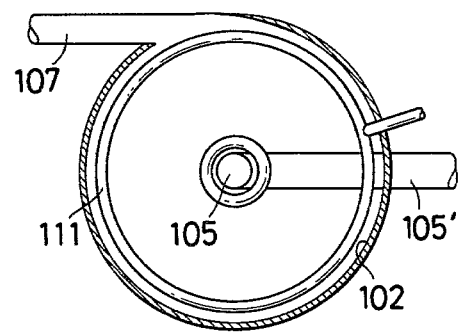
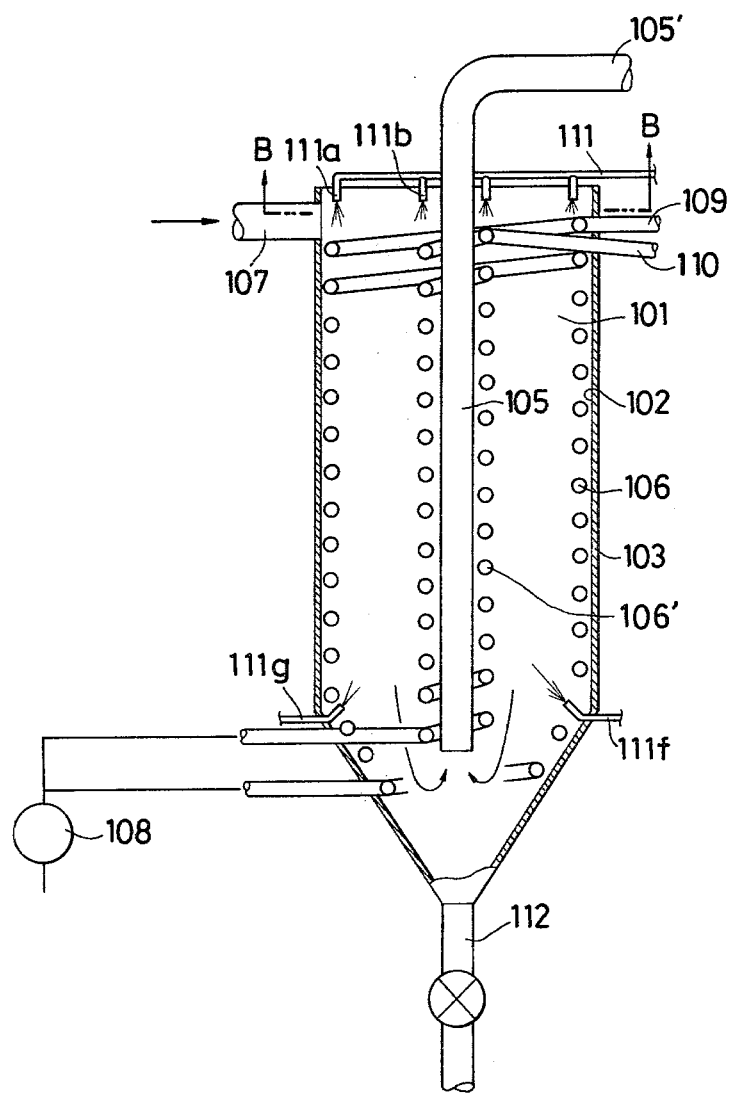

MICROBE-REMOVING AND AIR-CONDITIONING APPARATUS

OBJECT OF THE INVENTION

The present invention has an object to provide an apparatus which is able to remove microbes and produce an air of any desired temperature and humidity.

More particularly, the present invention has an object to provide a microbe-removing and air-conditioning apparatus for regulating an air appropriately for a room such as sickroom, operating room, aseptic working room, perishable foods-treating place, perishable foods-storage room, etc.

A further object of the present invention is to provide a microbe-removing and air-conditioning apparatus for removing microbes and smell from the air in a room, and regulating temperature and humidity as desired.

EXPLANATION OF THE INVENTION

The present invention relates to a microbe-removing and air-conditioning apparatus in which air is circulated from a room into a water-spraying cyclone where water is sprayed into said air to remove odor and separate dust and remove microbes and as well to make air humid, and the thus treated air is then fed to a temperature-regulating cyclone where water droplets are removed from the air and as well the temperature of the air is regulated.

As rooms to which the present invention is applied, there may be mentioned such rooms as sickroom, operating room, aseptic working room, general house, perishable foods-treating place, perishable foods-storage room or any other rooms.

Sickroom, operating room, aseptic working place and general house require an air from which microbes have been removed and which has been deodorized and is regulated at a temperature of about 22°–25° C. and at a humidity of about 50–70%, and perishable foods-treating place and perishable foods-storage room require an air from which microbes have been removed and which has been deodorized and is regulated at a temperature of about 0°–18° C. and at a humidity of about 70–100%.

According to the present invention, an air having such a desired temperature and humidity can be very easily produced. Namely it is possible to obtain an air having a humidity near the saturated humidity at a temperature of 0°–98° C. by previously adjusting the temperature of the water to be sprayed in the cyclone to a temperature of 0°–90° C. and by spraying the water of desired temperature within the range above. Thereafter the resulting air is fed to a temperature-regulating cyclone, and if the air is heated, the humidity thereof decreases with increasing the temperature thereof, and if the air is cooled, the air may be regulated to a desired temperature while maintaining saturated humidity. Accordingly, on the basis of the previously performed calculations, if only the temperature of the spraying water and the temperature in the temperature-regulating cyclone are set for obtaining a desired temperature and a desired humidity, it is possible to easily obtain an air of a desired constant temperature and humidity.

According to an water-spraying cyclone of the present invention, air may be circulated therein for a longer time and is subjected to the spraying of water of a temperature of 0°–98° C., and as a result dust, microbes and smell brought from the room can be removed and also the air is brought to nearly saturated humidity. In order to kill all or almost all of microbes, a sterilization cyclone may be provided between the room and the water-spraying cyclone and a high temperature water vapour may be fed into said sterilization cyclone.

The temperature-regulating cyclone according to the present invention may be such a cyclone that a temperature-regulated water vapour or air is fed in, but preferably use is made of such one that a conduit for temperature-regulating medium is circulated therein with an arrangement of one to three turns of the conduits. As said temperature-regulating medium, water at a temperature of 0°–40° C. may be used, and in the cyclone, an air of saturated humidity contacts with the conduit of 0°–40° C. for a sufficiently long time to regulate the air to a desired temperature. Excess water-droplets can be removed from the air by the applied centrifugal force during the revolution within the cyclone. If desired, it is possible to provide a water-removing cyclone between the water-spraying cyclone and the temperature-regulating cyclone for removal of water droplets from the air.

The room, the water-spraying cyclone and the temperature-regulating cyclone are successively connected together by means of circulating pipes so that the air can circulate through the whole system.

EXPLANATION OF THE DRAWINGS

FIG. 2 is an upper plan view f the cross section taken along the line A—A of the water-spraying cyclone of FIG. 1;

FIG. 3 is a longitudinal cross sectional view of another embodiment of the temperature-regulating cyclone; and FIG. 4 is an upper plan view of the cross section taken along the line B—B of FIG. 3.

With reference to FIG. 1, a room 1 is provided with an air conduit 3, through which the air in the room 1 is drawn out by means of a fan F, and blown into an water-spraying cyclone 6 through conduits 3' or 3". Before passing to the cyclone 6, excess air is discharged through an excess air discharge port 3-1. If necessary, the air may be caused to pass through a sterilization cyclone 4, which is provided with a vapour pipe 5, through which a vapour is ejected into the cyclone 4 to effect the sterilization of the air fed from the room 1. Thereafter the air is fed into the water-spraying cyclone 6 through the conduit 3". The air conduit 3" opens laterally into the spraying cyclone 6 at its downstream end and is connected with the cyclone 4 at its upstream end. The cyclone 6 has a return pipe 7 which opens upward and is fixed at the upper portion thereof. Around said return pipe 7 within the water-spraying cyclone 6 is coaxially mounted a water pipe 8 which has a great number of spraying nozzles 9a, 9b, . . . which open into the water-spraying cyclone 6, and the water pipe 8 is connected with a water tank 10. In the water tank 10 is always stored a great quantity of water which has been regulated to a given temperature within the range of 0°–98° C., and this water is ejected out by means of a pump P through the nozzles 9a, 9b, . . . in the form of fine droplets. As a result, the air fed into the water-spraying cyclone 6 contacts with these droplets from the nozzles 9a, 9b, . . . , and thereby causes a rapid and efficient heat-exchange therebetween, so that the air is regulated to a given temperature and as well odors, fine dust and microbes are caused to adhere to the wall of the cyclone and thus removed, and the air is caused to become saturated with moisture at about the same temperature as that of the water and the air then leaves through the return pipe 7.

Figure 1:
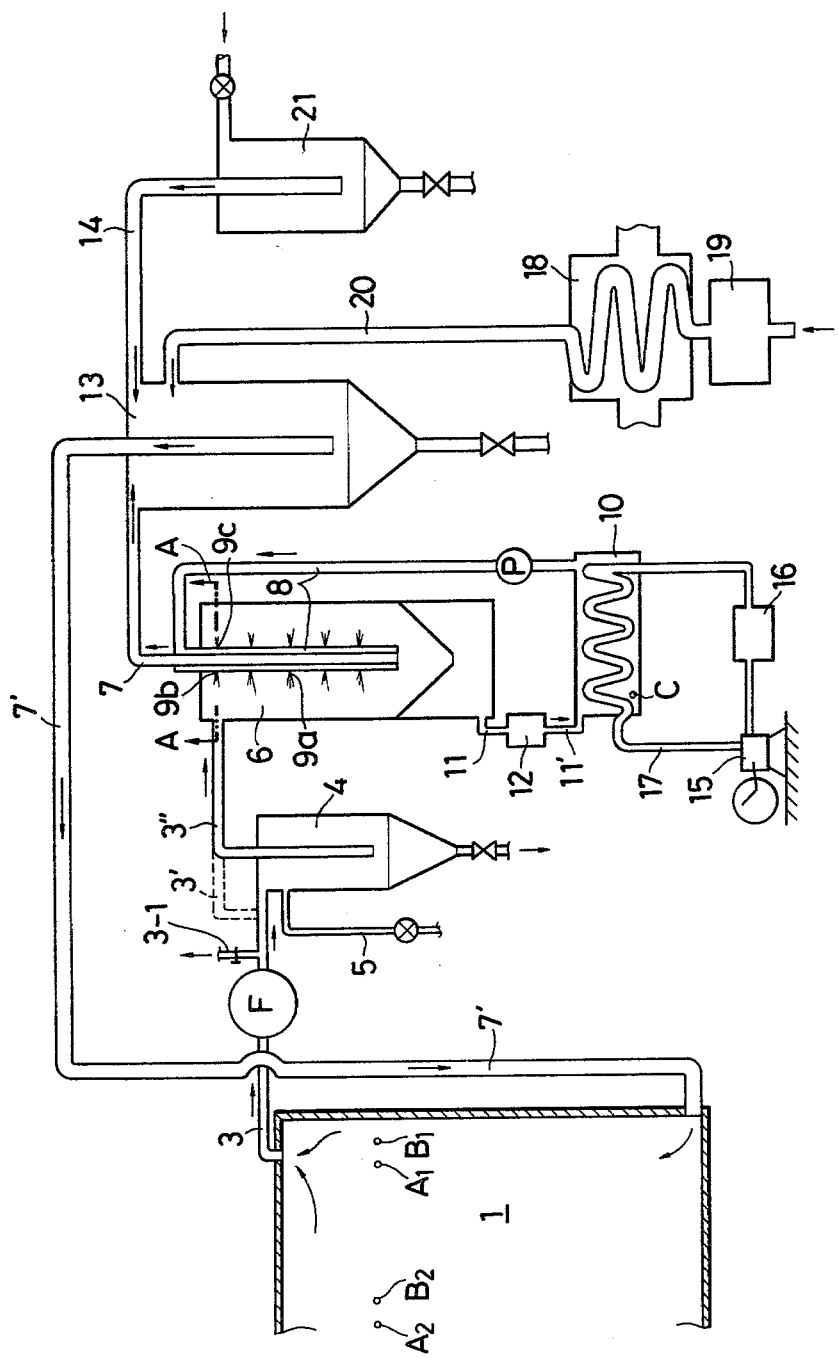
FIG. 1 is an explanatory view showing an arrangement of the microbe-removing and air-conditioning apparatus according to the present invention.

On the other hand, the sprayed water has odor components, fine dust particles, microbes, etc. dissolved or suspended therein, and since it is unsuitable for using repeatedly as it is, it is fed to a filter 12 through a conduit 11 to filter it and then fed back to the water tank 10 through a conduit 11'. To attain this treatment, the filter 12 may be preferably such conventional one which is further provided with a filter bed composed of a laminate of absorbents such as active carbon, diatomaceous earth, terra abla, ion-exchange resin etc. In such a way, the air is humidified to a saturated state at a lower temperature. Also, a compressor 15 for cooling water, a cooling machine 16 for gas leaving the compressor 15, and a conduit 17 for cooling the water within the water tank 10 from a closed cooling circuit. Also, in the case where the water is heated, a heater (not shown) may be provided, and if necessary, these cooling apparatus and heater may be used at the same time. The symbols $A_1$ and $A_2$ are temperature detectors provided in the room 1, $B_1$ and $B_2$ are humidity detectors, C is a temperature detector in the cooling water tank 10, and said temperature detectors $A_1$ and $A_2$ are electrically connected with the power source (not shown) of the fan F, and the temperature detector C is electrically connected with the compressor 15 or said heater.

The air of saturated humidity leaving the water-spraying cyclone 6 still includes more or less spray droplets therein. This air of saturated humidity is fed to the temperature-regulating cyclone 13 via the reflux pipe 7, in which cyclone the water droplets are completely removed from the air and at the same time the temperature of the air is also regulated therein. A vapour pipe 14, the downstream end of which opens to the cyclone 13, is provided so that vapour can be blown therein as desired, via cyclone 21, to heat the circulated air and thus cause the sterilization of the room 1 and the piping via a return pipe 7'.

The vapour pipe 14 is connected with the vapour cyclone 21, where the water droplets are removed so that only the vapour can be fed into the temperature-regulating cyclone 13. Namely, the vapour cyclone 21 is adapted to heat and humidify the air by the vapour when the temperature of the outside air is low. The temperature-regulating cyclone 13 also has a conduit 20 connected therewith, which permits the sterilized, heated, dry and fresh air to get in the second cyclone 13 through the filter 19 and a heating sterilization device 18. The heat exchanger 18 is a heating device which can be indirectly heated by vapour or other heating means and serves to heat the outside air when the temperature of the outside air is low. Namely, when the temperature of the outside air is as low as about 20° C., the fresh air sterilized at a temperature of 100°–110° C. by means of the heat exchanger 18 is introduced in the cyclone 13 thereby performing the regulation of temperature and humidity within the cyclone 13.

Another embodiment of the temperature-regulating cyclone according to the present invention is shown in FIGS. 3 and 4, wherein 101 shows a temperature-regulating cyclone, on the upper portion of which a return pipe 107 is mounted so as to be directed toward and tangentially of the cylindical inside face of the cyclone 101. 102 is the shell body of the cyclone 101 which is covered with an insulating material 103.

Also, at the central portion of the temperature-regulating cyclone 101 is mounted an air discharge pipe 105 in the vertical direction, which pipe is connected with an air conduit 105' mounted outside. Accordingly, the air from the return pipe 107 reaches the lower portion of the cyclone as it revolves therein, and rises in the air discharge pipe 105 from the lower portion thereof, thus moving in the arrow direction. Within the temperature-regulating cyclone 101 are mounted in the spirally wound form an outside piping 106 and an inside piping 106' and the lower ends of both the pipings 106 and 106' are connected to a pump 108, by means of which warm or cold water is caused to flow through said both pipings and to be discharged out of the upper discharge ports 109 and 110 respectively. At the upper and lower portions of the temperature-regulating cyclone 101, a number of water jet nozzles 111a and 111b of a washing water pipe 111 are provided so as to respectively direct to the parts over and below the upper and lower rows of the turns of the pipings 106 and 106' thereby allowing the washing water to be ejected to the inside faces of the pipings 106 and 106', the inside face of the shell body 102 and the outside face of the air discharging pipe 105. Also, at the lower portion of the cone portion of the shell body is provided a drain pipe 112 so that the washing water or a drain produced by cooling of the gas within the shell body can be discharged therethrough. Accordingly, the air from the return pipe 107 is allowed to be separated from dust, etc. by the effect of cyclone and heated or cooled to an appropriate temperature by means of the pipings 106 and 106' and thus produced air having a desired temperature and humidity is fed out through the air discharge pipe 105. Also, the separated dust, etc. can be washed by supplying water to the washing water pipe 111 and ejecting water jet from the nozzles 111a, 111b, . . . to be removed.

What is claimed is:

1. A microbe-removing and air-conditioning apparatus comprising a room;

a water-spraying cyclone, in which a return pipe is surrounded with a water pipe which has a plurality of spraying nozzles, said water-spraying cyclone comprising means through which the air in said room is circulated and in which water is sprayed and odor, fine dust and microbes are caused to adhere to the wall of the cyclone and removed, and the air is caused to become saturated with moisture;

a temperature-regulating cyclone in which a temperature-regulating medium conduit is spirally arranged within said cyclone, said temperature-regulating cyclone comprising means to remove water droplets from the humid air pressing from said water-spraying cyclone and means to regulate the temperature of the air; and a circulation pipe for feeding the air leaving the room to the water-spraying cyclone and from the water-spraying cyclone to the temperature-regulating cyclone and then back to the room therefrom; wherein upstream the water-spraying cyclone there is provided a sterilization cyclone where a high temperature vapour is introduced and mixed with the air coming from the room to effect sterilization.

2. A microbe-removing and air conditioning apparatus comprising a room;

a water-spraying cyclone, in which a return pipe is surrounded with a water pipe which has a plurality of spraying nozzles, said water-spraying cyclone comprising means through which the air in said room is circulated and in which water is sprayed and odor, fine dust and microbes are caused to adhere to the wall of the cyclone and removed, and the air is caused to become saturated with moisture;

a temperature-regulating cyclone in which a temperature-regulating medium conduit is spirally arranged within said cyclone, said temperature-regulating cyclone comprising means to remove water droplets from the humid air pressing from said water-spraying cyclone, and means to regulate the temperature of the air; and a circulation pipe for feeding the air leaving the room to the water-spraying cyclone and from the water-spraying cyclone to the temperature-regulating cyclone and then back to the room therefrom;

said water-spraying cyclone comprising an elongated vertically disposed cylindrical chamber, the axial length of which is substantially greater than the diameter thereof, said return pipe and said water pipe passing axially into said elongated chamber through the top thereof and extending to near the bottom thereof, said plurality of spraying nozzles being disposed along substantially the entire length of said water pipe and being disposed about the circumference thereof, and said circulation pipe for feeding air to the water-spraying cyclone having an exit end substantially tangent to the cylindrical said wall of and near the top of said cylindrical chamber.

* * * * *